United States Patent
Chen

(10) Patent No.: US 11,079,388 B2
(45) Date of Patent: Aug. 3, 2021

(54) SUPER-RESOLUTION IMMUNOFLUORESCENCE WITH DIFFRACTION-LIMITED PREVIEW

(71) Applicant: Ultivue, Inc., Cambridge, MA (US)

(72) Inventor: Xi Chen, West Newton, MA (US)

(73) Assignee: Ultivue, Inc., Cambridge, MA (US)

( * ) Notice: Subject to any disclaimer, the term of this patent is extended or adjusted under 35 U.S.C. 154(b) by 178 days.

(21) Appl. No.: 16/094,954

(22) PCT Filed: Apr. 25, 2017

(86) PCT No.: PCT/US2017/029279
§ 371 (c)(1),
(2) Date: Oct. 19, 2018

(87) PCT Pub. No.: WO2017/189498
PCT Pub. Date: Nov. 2, 2017

(65) Prior Publication Data
US 2019/0120847 A1 Apr. 25, 2019

Related U.S. Application Data

(60) Provisional application No. 62/327,604, filed on Apr. 26, 2016.

(51) Int. Cl.
*G01N 33/58* (2006.01)
*G01N 21/64* (2006.01)
*C07K 16/18* (2006.01)
*G01N 33/533* (2006.01)

(52) U.S. Cl.
CPC ........... *G01N 33/582* (2013.01); *C07K 16/18* (2013.01); *G01N 21/6458* (2013.01); *G01N 33/533* (2013.01)

(58) Field of Classification Search
CPC . G01N 33/582; G01N 33/533; G01N 21/6458
See application file for complete search history.

(56) References Cited

U.S. PATENT DOCUMENTS

| 7,932,060 B2 * | 4/2011 | Nadeau | C12Q 1/6804 435/91.2 |
|---|---|---|---|
| 2013/0261019 A1 | 10/2013 | Lin et al. | |
| 2014/0315189 A1 * | 10/2014 | Glezer | G01N 33/542 435/5 |

FOREIGN PATENT DOCUMENTS

| WO | 2012058638 A3 | 12/2012 |
|---|---|---|
| WO | 2013022694 A1 | 2/2013 |
| WO | 2014018675 A1 | 1/2014 |
| WO | 2014028538 A2 | 2/2014 |
| WO | 2014074597 A1 | 5/2014 |
| WO | 2015017586 A1 | 2/2015 |
| WO | 2015089506 A2 | 6/2015 |
| WO | 2015138231 A1 | 9/2015 |
| WO | 2015138653 A1 | 9/2015 |
| WO | 2017027370 A1 | 2/2017 |
| WO | 2017143006 A1 | 8/2017 |
| WO | 2018132392 A3 | 8/2018 |

OTHER PUBLICATIONS

Tang et al. "DNA Tetraplexes-Based Toehold Activation for Controllable DNA Strand Displacement Reactions" J. Am. Chem. Soc. 2013 vol. 135, p. 13628-13631. (Year: 2013).*
Green et al. "Toehold Switches: De-Novo-Designed Regulators of Gene Expression" Cell 2014 vol. 159, p. 925-939. (Year: 2014 ).*
Abe et al., Affinity labeling of vertebrate oxidosqualene cyclases with a tritiated suicide substrate, Biochem Biophys Res Commun. 187(1):32-8 (1992).
Beliveau et al., Single-molecule super-resolution imaging of chromosomes and in situ haplotype visualization using Oligopaint FISH probes, Nature Communications 6:4147 (13 pages), DOI: 10.1038/ncomms8147 (2015).
Bochet, Photolabile protecting groups and linkers, J. Chem. Soc., Perkin Trans. 1:125-142 (2002).
Bock, et al., Selection of single-stranded DNA molecules that bind and inhibit human thrombin, Nature, 335 (6360):564-6 (1992).
England et al., HaloTag Technology: A Versatile Platform for Biomedical Applications, Bioconjugate Chem. 26:975-986 (2015).
International Search Report and Written Opinion issued in PCT/US2017/029279, dated Aug. 7, 2017, 11 pages.
Jungmann et al. Multiplexed 3D Cellular Super-Resolution Imaging with DNA-PAINT and Exchange-PAINT, Nat Methods 11(3):313-318 (2014).
Kim et al., Molecular assembly for high-performance bivalent nucleic acid inhibitor, PNAS, 105(15):5664-5669 (2008).
Li et al., Inhibition of Cell Proliferation by an Anti-EGFR Aptamer, PLoS One, 6(6):1-10, e20299 (2011).

(Continued)

*Primary Examiner* — Changhwa J Cheu
(74) *Attorney, Agent, or Firm* — McNeill Baur PLLC

(57) ABSTRACT

An imaging agent comprises (a) at least one target recognition moiety; (b) at least one observable moiety non-transiently bound to the target recognition moiety, and (c) at least one docking moiety bound to the target recognition moiety, wherein the docking moiety is capable of transiently binding at least one observable moiety. In some embodiments, the at least one target recognition moiety is an antibody or antigen binding fragment thereof. A method of performing super-resolution imaging on a sample comprises (a) contacting the sample with at least one imaging agent comprising (i) a target-recognizing molecule non-transiently attached to at least one observable moiety and (ii) a target-recognizing molecule attached to at least one docking moiety, wherein the docking moiety is capable of transiently binding at least one observable moiety; (b) imaging the target-recognizing molecule non-transiently bound to at least one observable moiety; and (c) providing at least one observable moiety capable of transiently binding to the docking moiety and imaging the observable moiety transiently bound to the docking moiety.

20 Claims, 7 Drawing Sheets

Specification includes a Sequence Listing.

(56) References Cited

OTHER PUBLICATIONS

Maruani et al., A mild TCEP-based para-azidobenzyl cleavage strategy to transform reversible cysteine thiol labelling reagents into irreversible conjugates, Chem. Commun., 41:5279-5282 (2015).
Protein Interaction Analysis, BioRad Bulletin 119:1-6 (2013).
Sugita T. et al., Biochem Eng J 79:33-40 (2013).
Tasset et al., Oligonucleotide inhibitors of human thrombin that bind distinct epitopes, J. Mol. Biol. 272(5):688-98 (1997).
Thompson et al., SYNZIP Protein Interaction Toolbox: in Vitro and in Vivo Specification of Heterospecific Coiled-Coil Interaction Domains, ACS Synth. Biol. 1, 118-129 (2012).
Wolff et al., Breaking the Bonds: Non-viral Vectors Become Chemically Dynamic, Molecular Therapy, 16(1):8-15 (2008).
Xu et al., Directed Evolution of High-Affinity Antibody Mimics Using mRNA Display, Chemistry & Biology, 9:933-942 (2002).
Yan et al., Phys Chem Chem Phys. 11(29):6042-50, doi: 10.1039/b903544c (2009).
Yang, Haiou, Fc-binding hexamer peptide ligands for immunoglobulin purification, PhD Dissertation No. 3329367, North Carolina State University (2008).
Yoo et al., Identification of a Peptide Ligand for Antibody Immobilization on Biosensor Surfaces, BioChip J. 10(2):88-94 (2016).

\* cited by examiner

SEQUENCE LISTING

<160> NUMBER OF SEQ ID NOS: 11

<210> SEQ ID NO 1
<211> LENGTH: 19
<212> TYPE: DNA
<213> ORGANISM: Artificial Sequence

```
<220> FEATURE:
<223> OTHER INFORMATION: Nucleic acid strand conjugated to imaging agent
      (option 1)

<400> SEQUENCE: 1
tacctagatt acgattacg                                                   19

<210> SEQ ID NO 2
<211> LENGTH: 26
<212> TYPE: DNA
<213> ORGANISM: Artificial Sequence
<220> FEATURE:
<223> OTHER INFORMATION: Nucleic acid strand conjugated to imaging agent
      (option 2)

<400> SEQUENCE: 2
gctagtcgat gctagctagc tatgct                                           26

<210> SEQ ID NO 3
<211> LENGTH: 13
<212> TYPE: DNA
<213> ORGANISM: Artificial Sequence
<220> FEATURE:
<223> OTHER INFORMATION: Nucleic acid strand conjugated to
      non-transiently bound observable moiety (option 1)

<400> SEQUENCE: 3
cgtaatcgta atc                                                         13

<210> SEQ ID NO 4
<211> LENGTH: 19
<212> TYPE: DNA
<213> ORGANISM: Artificial Sequence
<220> FEATURE:
<223> OTHER INFORMATION: Nucleic acid strand conjugated to
      non-transiently bound observable moiety (option 2)

<400> SEQUENCE: 4
ctagctagca tcgactagc                                                   19

<210> SEQ ID NO 5
<211> LENGTH: 19
<212> TYPE: DNA
<213> ORGANISM: Artificial Sequence
<220> FEATURE:
<223> OTHER INFORMATION: Competitor nucleic acid strand (option 1)

<400> SEQUENCE: 5
cgtaatcgta atctaggta                                                   19

<210> SEQ ID NO 6
<211> LENGTH: 26
<212> TYPE: DNA
<213> ORGANISM: Artificial Sequence
<220> FEATURE:
<223> OTHER INFORMATION: Competitor nucleic acid strand (option 2)

<400> SEQUENCE: 6
agcatagcta gctagcatcg actagc                                           26

<210> SEQ ID NO 7
<211> LENGTH: 11
<212> TYPE: DNA
<213> ORGANISM: Artificial Sequence
<220> FEATURE:
<223> OTHER INFORMATION: Example 1 docking strand P1
```

```
<400> SEQUENCE: 7
ttatacatct a                                                               11

<210> SEQ ID NO 8
<211> LENGTH: 10
<212> TYPE: DNA
<213> ORGANISM: Artificial Sequence
<220> FEATURE:
<223> OTHER INFORMATION: Example 1 imager strand P1*
<220> FEATURE:
<221> NAME/KEY: modified base
<222> LOCATION: (10)..(10)
<223> OTHER INFORMATION: labelled with Cy3B fluorophore

<400> SEQUENCE: 8
ctagatgtat                                                                 10

<210> SEQ ID NO 9
<211> LENGTH: 12
<212> TYPE: DNA
<213> ORGANISM: Artificial Sequence
<220> FEATURE:
<223> OTHER INFORMATION: Example 2 docking strand

<400> SEQUENCE: 9
actgatttgg ct                                                              12

<210> SEQ ID NO 10
<211> LENGTH: 35
<212> TYPE: DNA
<213> ORGANISM: Artificial Sequence
<220> FEATURE:
<223> OTHER INFORMATION: Example 2 intermediate strand

<400> SEQUENCE: 10
actgatttgg ctttcggtag tagcttatac atcta                                     35

<210> SEQ ID NO 11
<211> LENGTH: 12
<212> TYPE: DNA
<213> ORGANISM: Artificial Sequence
<220> FEATURE:
<223> OTHER INFORMATION: Example 2 imager strand
<220> FEATURE:
<221> NAME/KEY: modified base
<222> LOCATION: (12)..(12)
<223> OTHER INFORMATION: labelled with Cy3B fluorophore

<400> SEQUENCE: 11
gccaaatcag tt                                                              12
```

SUPER-RESOLUTION IMMUNOFLUORESCENCE WITH DIFFRACTION-LIMITED PREVIEW

CROSS-REFERENCE TO RELATED APPLICATIONS

This application is a national phase entry pursuant to 35 U.S.C. § 371 of International Application No. PCT/US2017/029279, filed Apr. 25, 2017, which claims the benefit of priority of U.S. Provisional Application No. 62/327,604, filed Apr. 26, 2016, each of which is incorporated by reference herein in its entirety for any purpose.

SEQUENCE LISTING

The instant application contains a Sequence Listing submitted via EFS-Web in ASCII format and hereby incorporated by reference in its entirety. Said Sequence Listing, created on Dec. 12, 2018, is named 2018-12-12_01168-0003-00PCT_Replacement_Seq_List_ST25, and is 2,945 bytes in size.

DESCRIPTION

Field

This application provides for super-resolution immunofluorescence with diffraction-limited preview, including both reagents and methods for use therein.

Background

A series of super-resolution imaging techniques has significantly improved the resolution of optical microscopy beyond the diffraction limit One class of super-resolution imaging techniques is called stochastic super-resolution, which is characterized by images containing blinking or flickering signals from fluorescent labels. Depending on the method to process the data, stochastic super-resolution can be divided into single-molecule localization microscopy (SMLM) and super-resolution optical fluctuation imaging (SOFI). The blinking or flickering behavior can be achieved by several mechanisms such as photo-activation of organic dyes (e.g., in a technique widely known as stochastic optical reconstruction microscopy, or STORM), photo-switching of fluorescent proteins (e.g., in a technique widely known as photo activated localization microscopy, or PALM), and inherent blinking properties of quantum dots.

PAINT (point accumulation for imaging in nanoscale topography) is one extremely simple and powerful technique to achieve blinking or flickering signals from fluorescent labels, which is caused by dynamic and transient noncovalent interactions between a non-observable docking site attached to a target-recognizing molecule and an observable molecule in solution. PAINT-based super-resolution imaging has been adopted to immunofluorescence by Jungmann et al., Nat methods 11(3):313-8 (2014) (Ref: PMID 24487583), where an antibody is used as the target-recognizing molecule. Here we call this technique PAINT-based Super-resolution Immunofluorescence (PSRIF). In the particular embodiment carried out by Jungmann et al., a short DNA oligonucleotide (called the docking strand) is used as the docking site, and a fluorophore-labeled DNA oligonucleotide (called the imager strand) with sequence complementary to the docking strand is used as the observable molecule.

As with other stochastic super-resolution imaging techniques, PSRIF collects multiple images over a period of time (known as 'taking the blinking movie') and reconstructs them into the final image with a computer. One drawback of PSRIF is that, in most cases, before taking the blinking movie and reconstructing the image (which usually takes >10 min), the user cannot obtain a comprehensive image of the sample to evaluate whether the sample being imaged is appropriate.

For example, the sample being imaged may be of low quality or may not be in fact the desired sample. For instance, if a person conducting the imaging wishes to visualize a particular cell type, that cell type may or may not be in the field of view. Alternatively, there may be quality problems with the cell in the field of view, such as inadequate or ineffective staining.

Because PSRIF relies on collecting many multiple images over a period of time, experimental resources, computing time and elapsed time can be wasted if the sample is not adequate or correct for the experiment being performed.

Therefore, the art requires improved methods for PSRIF that allow for a preview of the sample before super-resolution imaging begins.

SUMMARY

In accordance with the description, in some embodiments an imaging agent comprises (a) at least one target recognition moiety; (b) at least one observable moiety non-transiently bound to the target recognition moiety, and (c) at least one docking moiety bound to the target recognition moiety, wherein the docking moiety is capable of transiently binding at least one observable moiety.

In some embodiments, the at least one target recognition moiety is an antibody or antigen binding fragment thereof. In some embodiments, the observable moiety non-transiently bound to the target recognition moiety is a signal-emitting moiety. In some embodiments, the signal-emitting moiety is an organic small molecule. In some embodiments, the organic small molecule is a fluorophore.

In some embodiments, the observable moiety non-transiently bound to the target recognition moiety is directly attached to the target recognition moiety. In some embodiments, the observable moiety non-transiently bound to the target recognition moiety is indirectly attached to the target recognition moiety. In some embodiments, the observable moiety non-transiently bound to the target recognition moiety is directly attached to the docking moiety.

In some embodiments, the observable moiety non-transiently bound to the target recognition moiety is bound covalently. In some embodiments, the docking moiety is attached to the imaging agent covalently. In some embodiments, the observable moiety non-transiently bound to the target recognition moiety is bound noncovalently. In some embodiments, the docking moiety is attached to the imaging agent noncovalently. In some embodiments, the observable moiety non-transiently bound to the target recognition moiety is bound through a streptavidin-biotin interaction. In some embodiments, the observable moiety non-transiently bound to the target recognition moiety is bound through a nucleic acid-nucleic acid interaction.

In some embodiments, (a) the nucleic acid bound to the observable moiety is longer than the nucleic acid bound to the target recognition moiety or (b) the nucleic acid bound to the target recognition moiety is longer than the nucleic acid bound to the observable moiety, and wherein the single-stranded portion of the longer nucleic acid serves as a toehold for displacement of the shorter strand.

In some embodiments, the docking moiety comprises nucleic acids. In some embodiments, the target recognition moiety is an antibody or antigen binding fragment thereof, an aptamer, or an oligonucleotide. In some embodiments, both the observable moiety non-transiently bound to the target recognition moiety and the observable moiety transiently bound to the target recognition moiety are attached to a single target recognition moiety. In some embodiments, the observable moiety non-transiently bound to the target recognition moiety and the observable moiety transiently bound to the target recognition moiety are attached to different target recognition moieties, wherein: (a) the different target recognition moieties bind to the same epitope on a target; (b) the different target recognition moieties bind to different epitopes on the same target; (c) the different target recognition moieties bind to different proteins, optionally wherein the proteins are capable of interacting with each other.

In some embodiments a method of performing super-resolution imaging on a sample comprises: (a) contacting the sample with at least one imaging agent comprising (i) a target-recognizing molecule non-transiently attached to at least one observable moiety and (ii) a target-recognizing molecule attached to at least one docking moiety, wherein the docking moiety is capable of transiently binding at least one observable moiety; (b) imaging the target-recognizing molecule non-transiently bound to at least one observable moiety; and (c) providing at least one observable moiety capable of transiently binding to the docking moiety and imaging the observable moiety transiently bound to the docking moiety.

In some embodiments of the method, the target-recognizing molecule is an antibody or antigen binding fragment thereof. In some embodiments of the method, the imaging agent is the imaging agent in any of the embodiments described herein. In some embodiments of the method, the method further comprises removing or inactivating the observable moiety non-transiently attached to the target recognizing molecule. In some embodiments of the method the observable moiety is inactivated by chemical bleaching. In some embodiments of the method, the observable moiety is inactivated by photo bleaching. In some embodiments of the method, the observable moiety is removed by introducing a competitor molecule. In some embodiments of the method, the observable moiety is removed by nucleic acid strand displacement. In some embodiments of the method, the observable moiety is inactivated by introducing a fluorescence quencher.

In some embodiments, a method of performing super-resolution imaging comprises (a) providing the imaging agent of any one the embodiments described herein; (b) obtaining a preview image using the at least one observable moiety non-transiently bound to the target recognition moiety; (c) assessing the preview image; and (d) obtaining a super-resolution image using at least one observable moiety transiently bound to a docking moiety.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

In FIGS. 2A-F, the filled star denotes a non-transiently attached observable moiety, and the thick curved line denotes a docking moiety. The ladder-like structure denotes a nucleic acid duplex.

In FIGS. 3A and 3B, the non-transiently attached observable moiety is attached to the target recognition moiety through a non-covalent interaction between moieties X and Y (e.g., X can be a chemical compound such as biotin and Y can be a binder of the chemical compound such as streptavidin, or vice versa). This linkage can be reversed by outcompeting binding by adding a competing molecule, which can be either X or Y, or variants of either X or Y. FIGS. 3C and 3D show a particular embodiment of the scheme shown in FIGS. 3B and 3A, respectively, where the X and Y are two oligonucleotides with partially complementary sequences, and the non-transiently attached observable moiety can be displaced from the target recognition moiety by using a nucleic acid having a toehold for binding to either the strand affixed to the non-transiently attached observable moiety (FIG. 3C) or the strand affixed to the target recognition moiety (FIG. 3D). FIG. 3E shows an embodiment where the target recognition moiety (here an antibody) and the non-transiently attached observable moiety are attached via a labile (e.g., photolabile) bond, denoted by the open circle. The labile bond can be cleaved by physical or chemical intervention (e.g., UV irradiation). The two open semicircles denote the remnant of such cleavage. FIG. 3F shows an embodiment where the non-transiently attached observable moiety is inactivated by physical or chemical intervention such as chemical bleaching or photobleaching. The open star denotes the inactivated, formerly observable moiety. Alternatively, the wavelength of emission of the observable moiety can be shifted, e.g. via a cis-trans isomerization. An example of a fluorophore that emits at different wavelengths in the cis and trans configurations is found in Yan et al., Phys Chem Chem Phys. 11(29):6042-50 (2009) (doi: 10.1039/b903544c). FIG. 3G shows an embodiment where the observable moiety non-transiently attached to the target recognition moiety is inactivated by introducing a quencher moiety before performing the super-resolution imaging.

DESCRIPTION OF THE SEQUENCES

Figure 1:
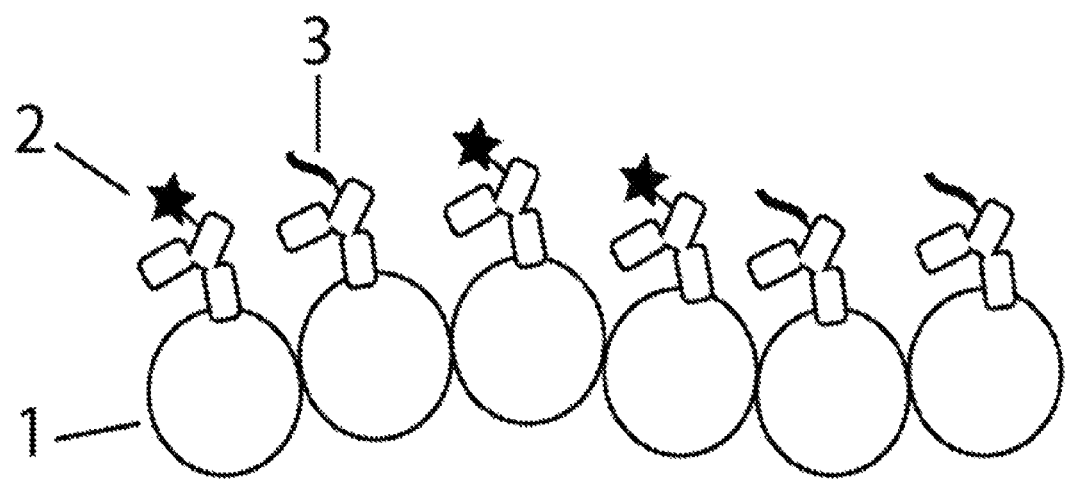
FIG. 1 illustrates certain imaging agents. In some embodiments, the non-transiently attached observable moiety is attached to one target recognition moiety, whereas the docking moiety is attached to a different target recognition moiety. Such an approach may be represented by two antibodies. In such a two antibody approach, as shown in FIG. 1, 1 denotes the target, 2 denotes a non-transiently attached observable moiety (here a fluorescent dye stably attached to the antibody), and 3 denotes a docking moiety. The sample represented has multiple molecules of the target and some of each type of antibody bind to molecules of the target.

The following table describes certain sequences referenced in this application.

TABLE 1

Sequences

| Description | Sequence | SEQ ID NO |
|---|---|---|
| Nucleic acid strand conjugated to imaging agent (option 1) (source: artificial) | 5'-TACCTAGATTACGATTACG-3' | 1 |
| Nucleic acid strand conjugated to imaging agent (option 2) (source: artificial) | 5'-GCTAGTCGATGCTAGCTAG CTATGCT-3' | 2 |
| Nucleic acid strand conjugated to non-transiently bound observable moiety (option 1) (source: artificial) | 5'-CGTAATCGTAATC-3' | 3 |
| Nucleic acid strand conjugated to non-transiently bound observable moiety (option 2) (source: artificial) | 5'-CTAGCTAGCATCGACTAGC-3' | 4 |
| Competitor nucleic acid strand (option 1) (source: artificial) | 5'-CGTAATCGTAATCTAGGTA-3' | 5 |
| Competitor nucleic acid strand (option 2) (source: artificial) | 5'-AGCATAGCTAGCTAGCATCG ACTAGC-3 | 6 |
| Example 1 docking strand P1 (source: artificial) | 5'-TTATACATCTA-3' | 7 |
| Example 1 imager strand P1* (source: artificial) | 5'-CTAGATGTAT-Cy3B-3' | 8 |
| Example 2 docking strand (source: artificial) | 5'-ACTGATTTGGCT-3' | 9 |
| Example 2 intermediate strand (source: artificial) | 5'-ACTGATTTGGCTTTCGGTAGTA GCTTATACATCTA-3' | 10 |
| Example 2 imager strand (source: artificial) | 5'-GCCAAATCAGTT-Cy3B-3' | 11 |

DESCRIPTION OF THE EMBODIMENTS

I. Improved Imaging Agents for Use in PSRIF

In one embodiment, an imaging agent comprises (a) a target recognition moiety; (b) at least one observable moiety non-transiently bound to the target recognition moiety; and (c) at least one docking moiety bound to the target recognition moiety, wherein the docking moiety is capable of transiently binding at least one observable moiety.

Transient binding refers to a binding interaction where at least one of the following is true (1) the dissociation rate constant of the bound complex (often expressed as $k_{off}$) is 0.1 s$^{-1}$ or higher or (2) the dissociation constant (often expressed $K_d$) is 100 nM or higher.

Non-transient binding refers to a binding interaction where dissociation rate constant of the bound complex ($k_{off}$) is lower than 0.1 s$^{-1}$, AND the dissociation constant ($K_d$) is lower than 100 nM.

A. Target Recognition Moiety

The target recognition moiety refers to antibodies and antibody-like molecules that can be used to detect the target molecule. Antibody refers to any immunoglobulin from any species that can specifically recognize a target molecule. Antibody-like molecule refers to (Class A) any engineered variation or fragment of an antibody such as Fab, Fab', F(ab')$_2$, single heavy chain, diabody, and the like (antigen binding fragments of antibodies) (Class B) any known binding partner of a target molecule and engineered variants of such binding partner, (Class C) any binding partner of the target molecule engineered via directed evolution (e.g., peptides and aptamers), and (Class D) any molecule that selectively forms covalent bond(s) with a target (e.g., a suicide substrate of an enzyme of interest).

Table 2 provides a representative listing of targets and corresponding target recognition moieties.

TABLE 2

Representative Targets and Target Recognition Moieties

| Target | Target Recognition Moiety | Source or Sequence |
|---|---|---|
| Any protein | Antibody (Class A) | Variable |
| Fluorocein (chemical compound) | Antibody (Class A) | Abcam, product # ab7253 |
| Digoxigenin (chemical compound) | Antibody (Class A) | Abcam, product # ab76907 |
| Biotin | Avidin/Streptavidin (Class B) | |
| Epidermal growth factor receptor (EGFR, protein) | Epidermal growth factor (EGF, Class B) | |
| Platelet-derived growth factor receptor (PDGFR, protein) | Platelet-derived growth factor (PDGF, Class B) | |
| Epidermal growth factor receptor (EGFR, protein) | E07 aptamer (Class C) | Li et al., PLoS ONE, 2011; 6(6): e20299 |
| Integrins (protein) | RGD-containing peptides (Class B) | |
| TNF-α (protein) | T09.12 peptide (Class C) | Xu et al., Chem Biol. 2002 Aug; 9(8): 933-42. |
| HaloTag (enzyme) | Halogenated compounds (Class D) | Bioconjug Chem. 2015 Jun. 17; 26(6): 975-86. |
| Oxidosqualene cyclase (OSC, enzyme) | [3H]29-methylidene-2,3-oxidosqualene ([3H]29-MOS, Class D) | Biochem Biophys Res Commun. 1992 Aug. 31; 187(1): 32-8. |

In some embodiments, both the observable moiety non-transiently bound to the target recognition moiety and the observable moiety transiently bound to the target recognition moiety are attached to a single target recognition moiety. This is called the one-target-recognition-moiety embodiment.

In other embodiments, the observable moiety non-transiently bound to the target recognition moiety and the observable moiety transiently bound to the target recognition moiety are attached to different target recognition moieties, wherein: (a) the different target recognition moieties bind to the same epitope on a target; (b) the different target recognition moieties bind to different epitopes on the same target; (c) the different target recognition moieties bind to different proteins, optionally wherein the proteins are capable of interacting with each other. For example, if the user desires to image microtubules in order to study mitosis, one target recognition moiety may be an antibody against α-alpha tubulin and the other target recognition moiety may be an antibody against β-tubulin. As another example, the two antibodies may be chosen that bind to the same organelle that the user wishes to image, for example, two antibodies that bind to mitochondria. These are called the two-target-recognition-moiety embodiment. In such an embodiment, a user may adjust the concentration of each antibody and staining time to achieve optimal staining and imaging performance. If the two target recognition moieties recognize the same epitope and are introduced to the sample sequentially, the user may ensure the first moiety does not occupy all targets or all binding sites on the target, which can be achieved by limiting the concentration and/or staining time.

B. At Least One Observable Moiety Non-Transiently Bound to the Target Recognition Moiety 1. Description of Observable Moieties Non-Transiently Bound Various observable moieties may be non-transiently bound to the target recognition moiety. In some embodiments, any observable moiety may be employed and in some embodiments the moiety is optically observable. The moiety may be signal absorbing or signal emitting. Of signal emitting molecules, molecules that fluoresce may be used, such as organic small molecules, including, but not limited to fluorophores, such as, but not limited to, fluorescein, Rhodamine, cyanine dyes, Alexa dyes, DyLight dyes, Atto dyes, etc.

In some embodiments organic polymers, such as p-dots may be employed. In some embodiments, the observable moiety may be a biological molecule, including but not limited to a fluorescent protein or fluorescent nucleic acid (including fluorescent RNAs including Spinach and its derivatives). In some embodiments, the observable moiety may be an inorganic moiety including Q-dots. In some embodiments, the observable moiety may be a moiety that operates through scattering, either elastic or inelastic scattering, such as nanoparticles and Surface Enhanced Raman Spectroscopy (SERS) reporters (e.g., 4-Mercaptobenzoic acid, 2,7-mercapto-4-methylcoumarin). In some embodiments, the observable moiety may be chemiluminascence/electrochemiluminescence emitters such as ruthenium complexes and luciferases. The observable moiety may generate an optical signal, an electromagnetic signal (across the entire electromagnetic spectrum), atomic/molecular mass (e.g. detectable by mass spectrometry), tangible mass (e.g., detectable by atomic force microscope), current or voltage.

2. Options for Non-Transient Binding

Different strategies may be employed for non-transient binding of an observable moiety to the target recognition moiety.

In some embodiments, the observable moiety non-transiently bound to the target recognition moiety is directly attached to the target recognition moiety and in other embodiments it is indirectly attached to the target recognition moiety, such as through a linker. In some embodiment, the observable moiety non-transiently bound to the target recognition moiety is directly attached to the docking moiety, and in another embodiment, the observable moiety non-transiently bound to the target recognition moiety is indirectly attached to the docking moiety.

In some embodiments, the observable moiety non-transiently bound to the target recognition moiety may be covalently bound to either the target recognition moiety, a linker, or the docking moiety. In other embodiments, the observable moiety non-transiently bound to the target recognition moiety may be noncovalently bound to either the target recognition moiety, a linker, or the docking moiety.

Examples of noncovalent binding include as nucleic acid hybridization, protein-protein interaction, protein-peptide interaction, protein-small-molecule interaction including biotin-(strept)avidin interaction.

If noncovalent binding is desired, the observable moiety may be bound through a streptavidin-biotin interaction. In one embodiment, strepatavidin may be conjugated to the observable moiety and in another embodiment, biotin may be conjugated to the observable moiety. When the biotin or streptavidin, respectively, is bound to the imaging agent, it may be bound to the imaging agent on the target recognition moiety, the docking site, or a linker.

In one embodiment, either streptavidin or biotin may be used to compete away the observable moiety. In these embodiments, wildtype streptavidin and biotin maybe used. In other embodiments, mutant or engineered forms of streptavidin and biotin may be employed that have either higher or lower affinities for each other than wildtype. In this way, the streptavidin or biotin that has the higher affinity may be added to compete away the observable moiety. See FIG. 3A-B.

TABLE 3

Noncovalent Non-transient Attachment Embodiments

| Moiety conjugated to imaging agent | Moiety conjugated to non-transiently bound observable moiety | Competitor moiety |
|---|---|---|
| biotin | Avidin/streptavidin/neutravidin | |
| dethiobiotin | Avidin/ streptavidin/neutravidin | biotin |

TABLE 3-continued

Noncovalent Non-transient Attachment Embodiments

| Moiety conjugated to imaging agent | Moiety conjugated to non-transiently bound observable moiety | Competitor moiety |
|---|---|---|
| biotin | Anti-biotin antibody | Streptavidin |
| biotin | Streptavidin variants with reduced affinity (Source: U.S. Pat. No. 6,207,390 B1) | Wildtype streptavidin |
| Leucine zipper | Complementary leucine zipper (Source: ACS Synth Biol. 2012 Apr 20; 1(4): 118-129.) | |
| Leucine zipper | Truncated complementary leucine zipper | Full-length complementary leucine zipper |
| Thrombin | Thrombin aptamer (TBA or HD22) (Source: Nature. 1992 Feb 6; 355(6360): 564-6.; J Mol Biol. 1997 Oct 10; 272(5): 688-98.) | |
| Thrombin | Thrombin aptamer TBA | Thrombin aptamer TBA-HD22 fusion (Source: Proc Natl Acad Sci USA. 2008 Apr. 15; 105(15): 5664-9.) |

**Note the examples in the first column and the second column may be switched.

In some embodiments, the observable moiety is non-transiently bound to the target recognition moiety through a nucleic acid-nucleic acid interaction. In some embodiments either (a) the nucleic acid bound to the observable moiety is longer than the nucleic acid bound to the target recognition moiety or (b) the nucleic acid adjacent to the target recognition moiety is longer than the nucleic acid adjacent to the observable moiety, and the longer nucleic acid serves as a toehold for displacement of the shorter strand. See FIG. 3C-3D. In some embodiments, the longer sequence has from about 2 to about 20, from about 5 to about 15, or from about 6 to about 10 more nucleic acids (i.e., the length of the toehold). In some embodiments, the toehold is about 2, 4, 5, 6, 7, 8, 9, 10, 15, or 20 nucleic acids long. The sequence of these nucleic acids can be arbitrary, as long as unwanted secondary structure and unwanted interaction with endogenous nucleic acid are minimized. Several computational tools, such as mfold, NUPACK, BLAST can assist this task.

TABLE 4

Toehold Embodiments

| Nucleic acid strand conjugated to imaging agent | Nucleic acid strand conjugated to non-transiently bound observable moiety | Competitor nucleic acid strand |
|---|---|---|
| 5'-TACCTAGATTACGATTACG-3' (SEQ ID NO: 1) | 5'-CGTAATCGTAATC-3' (SEQ ID NO: 3) | 5'-CGTAATCGTAATCTAGGTA-3' (SEQ ID NO: 5) |
| 5'-GCTAGTCGATGCTAGCTAGCTATGCT-3' (SEQ ID NO: 2) | 5'-CTAGCTAGCATCGACTAGC-3' (SEQ ID NO: 4) | 5'-AGCATAGCTAGCTAGCATCGACTAGC-3 (SEQ ID NO: 6) |

In some embodiments, the observable moiety non-transiently bound to the target recognition moiety may be conjugated by homo- or hetero-bifunctional cross linkers, such as succinimidyl 4-(N-maleimidomethyl)cyclohexane-1-carboxylate (SMCC), Sulfo-SMCC, SM-PEGn, and many other examples described in Chapters 4, 5, and 6 of Bioconjugate Techniques (Third Edition) (ISBN: 978-0-12-382239-0). Conjugation of such cross linkers, as well as their removal, has been described previously.

Figure 3:
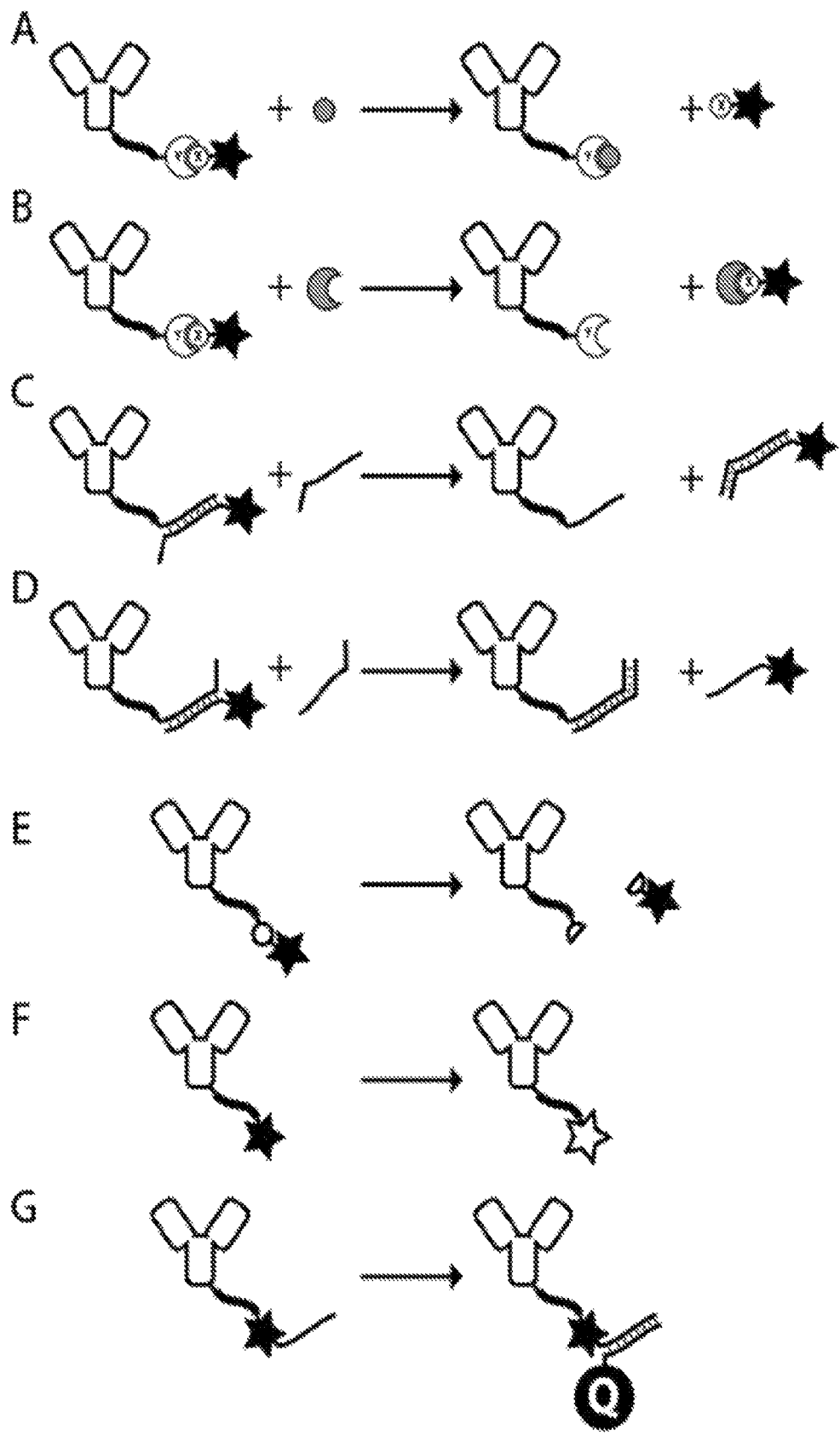
FIGS. 3A-G show various methods for removing or inactivating the non-transiently attached observable moiety before performing PAINT or another type of super-resolution immunofluorescence.
Figure 4:
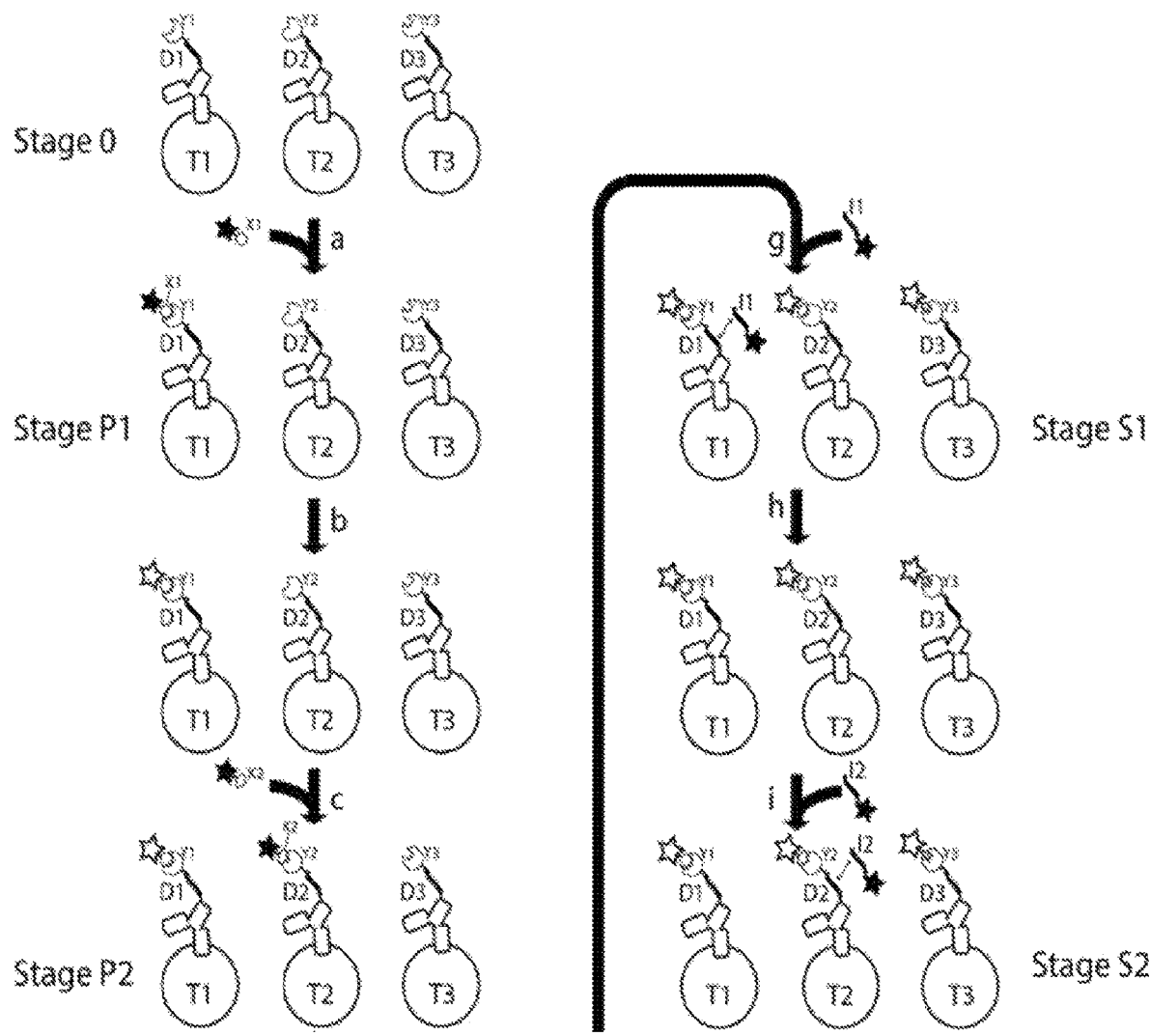
FIG. 4 illustrates one example of multiplexed preview followed by multiplexed PAINT. In this example, 3 targets are to be imaged in both diffraction-limited preview and in super-resolution, and inactivation of non-transiently attached observable signal (here photobleaching of a fluorophore) is used to terminate the preview of each target (Steps b, d, and f). Many other methods for terminating the preview of the target are described in Section II.B; methods for removing or inactivating an observable moiety are also disclosed in PCT/US2015/020034 or PCT/US2013/054798. At Stage 0, all three targets are simultaneously stained with their corresponding antibody attached to at least one docking moiety (D1, D2 or D3) and at least one adaptor moiety to attach the non-transiently attached observable moiety (Y1, Y2 or Y3). Then an observable moiety (here a fluorophore) linked to an adaptor X1 can be added to the sample (Step a). Optionally, the unbound X1-linked observable moiety can be washed away. Then the diffraction-limited preview of the first target (T1) can be obtained (Stage P1). Next, the observable moiety non-transiently attached to the antibody against T1 via the X1-Y1 interaction is photobleached (Step b). These steps can be repeated for the second target (T2, with Steps c and d), whose preview is obtained in Stage P2, and the third target (T3, with Steps e and f), whose preview is obtained in Stage P3, using appropriate reagents as shown. After the preview of all 3 targets, imager strand I1 can be added (Step g) to image T1 in super-resolution (Stage S1), after which I1 can be washed away (Step h). These steps can be repeated for T2 (Steps i and j), whose super-resolution image is obtained in Stage S2, and T3 (Step k), whose super-resolution image is obtained in Stage S3. The workflow shown here is flexible and steps can be taken in different order. For example, one may obtain the diffraction-limited previews in the order of T3→T2→T1, instead of T1→T2→T3. One may also follow Stage P1 with Stage S1 by performing Step g after Step b.
Figure 4:
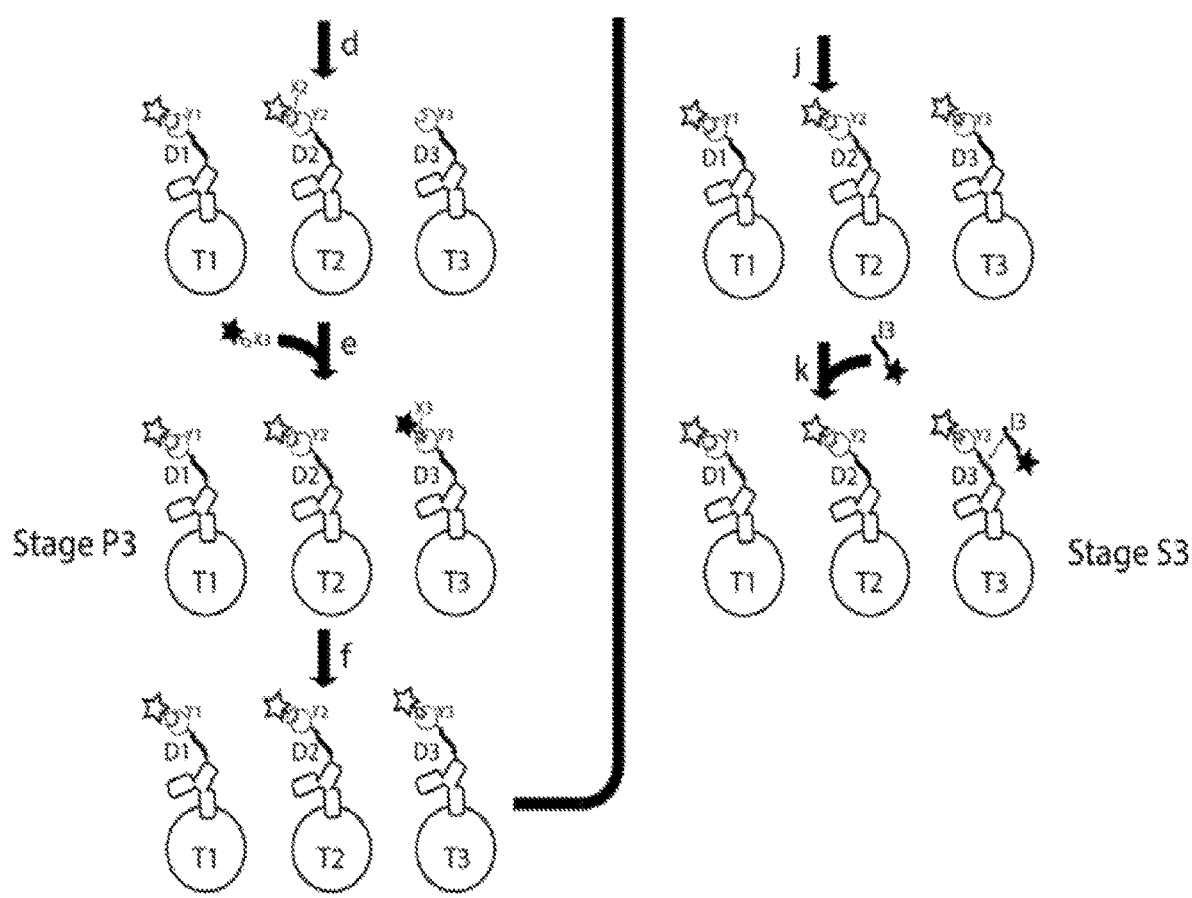

The observable moiety non-transiently bound to the target recognition moiety may also be conjugated by a labile bond (for example, a photolabile bond), such as is shown in FIG. 3E, wherein the labile bond or photolabile bond can be cleaved by physical or chemical intervention (for example, in the case of a photolabile bond, by UV irradiation). Photolabile linkers are disclosed in Bochet, J. Chem. Soc., Perkin Trans. 1:125-142 (2002). Other labile bonds include disulfide bonds (cleavable by Dithiothreitol (DTT), tris(2-carboxyethyl)phosphine (TCEP)), 2-nitrobenzyl bonds (cleavable by UV irradiation); ribonucleotide bonds (cleavable by RNase), deoxyuridine bonds (cleavable by USER Enzyme mix (New England Biolabs, Cat #M5505S)), bridging phosphothiolate bonds (cleavable by silver ion); para-azidobenzyl bonds (cleavable by TCEP (Maruani et al., Chem. Commun. 51:5279-5282 (2015)).

C. At Least One Docking Moiety

In some embodiments, the docking moiety is a nucleic acid, a protein, a peptide, or a chemical compound. Many proteins and domains of proteins are known to interact with other proteins, domains or peptides. Some of the best known domains include SH2, SH3, and WD40 domains. In many cases the binding partner of these proteins and domains are known and can be engineered to have the desired affinity. For example, if the affinity of the binding is too high to be transient, residues of the binding partner can be mutated and/or truncated. In some cases, a native binding pair from one organism (e.g. yeast) can be used to study samples from another organism (e.g., human) to avoid cross interaction. Many chemical compounds can make specific interactions with other compounds or proteins, where the affinity is either directly suitable for PSRIF or can be engineered to be suitable for PSRIF. For example, biotin and avidin/streptavidin interact with sufficient specificity. Even though the affinity of native biotin and avidin/streptavidin is too high to provide transient binding for for PSRIF, variants of biotin that bind avidin/streptavidin less stably (e.g., dethiobiotin) and variants of avidin/streptavidin that bind biotin less stably have been readily described. Many other chemical compounds, such as digoxigenin, fluorescein, tacrolimus and rapamycin also have well known binding partners.

In some embodiments, the docking moiety comprises nucleic acids. In some embodiments, the nucleic acids are single stranded nucleic acids such as single stranded DNA, RNA, or a nucleic acid analog. A nucleic acid analog may include an altered phosphate backbone, an altered pentose sugar, and/or altered nucelobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the docking moiety is attached to the imaging agent covalently and in other embodiments noncovalently.

In some embodiments, the docking moiety comprises single-stranded nucleic acids and may be from about 5 to 20 nucleic acids long, from about 8 to 15, or from about 10 to 12 nucleic acids long. In some embodiments, the docking moiety is about 5, 8, 9, 10, 11, 12, 13, 14, 15, 18, or 20 nucleic acids long.

The docking moiety may be an independent element or it may be part of the target recognizing moiety. For example, if the target recognizing moiety is an antibody, part of the Fc domain of the antibody may be the docking moiety and a peptide or protein that transiently binds the Fc domain may be used to achieve transient binding. For example, mutating or deleting key residues or fragments of protein A or protein G can lead to variants of the such proteins that have reduced affinity to Fc domain and bind the Fc domain transiently. Such peptides can also be obtained by systematic searching or directed evolution as described in Sugita T. et al., Biochem Eng J 79:33-40 (2013); Yang, Haiou, Fc-binding hexamer peptide ligands for immunoglobulin purification, PhD Dissertation No. 3329367, North Carolina State University (2008); Yoo R-J. et al., BioChip J 1-7 (2015).

D. At Least One Observable Moiety Transiently Bound to the Docking Moiety

1. Observable Moiety Transiently Bound

Various observable moieties may be transiently bound to the target recognition moiety. In some embodiments, any observable moiety may be employed and in some embodiments the moiety is optically observable. The moiety may be signal absorbing or signal emitting. Of signal emitting molecules, molecules that fluoresce may be used, such as organic small molecules, including, but not limited to fluorophores, such as, but not limited to, fluorescein, Rhodamine, cyanine dyes, Alexa dyes, DyLight dyes, Atto dyes, etc.

In some embodiments organic polymers, such as p-dots may be employed. In some embodiments, the observable moiety may be a biological molecule, including but not limited to a fluorescent protein or fluorescent nucleic acid (including fluorescent RNAs including Spinach and its derivatives). In some embodiments, the observable moiety may be an inorganic moiety including Q-dots. In some embodiments, the observable moiety may be a moiety that operates through scattering, either elastic or inelastic scattering, such as nanoparticles and Surface Enhanced Raman Spectroscopy (SERS) reporters (e.g., 4-Mercaptobenzoic acid, 2,7-mercapto-4-methylcoumarin). In some embodiments, the observable moiety may be chemiluminascence/electrochemiluminescence emitters such as ruthenium complexes and luciferases. The observable moiety may generate an optical signal, an electromagnetic signal (across the entire electromagnetic spectrum), atomic/molecular mass (e.g. detectable by mass spectrometry), tangible mass (e.g., detectable by atomic force microscope), current or voltage.

In some embodiments, the observable moiety non-transiently bound to the target recognition moiety can be the same type of observable moiety as the one transiently bound to the docking moiety. In some embodiments, they may be different.

2. Options for Transient Binding and Imager Moiety

In some embodiments, an imager moiety allows for transient binding between the observable moiety and the docking moiety.

In some embodiments, the docking moiety may be a nucleic acid strand. In such cases, the observable moiety may be conjugated to an imager moiety, which may be a nucleic acid strand that is complementary to the docking strand to allow for transient binding. In such a case, the observable moiety may be conjugated to an imager moiety that may be from about 5 to 20 nucleic acids long, from about 8 to 15, or from about 10 to 12 nucleic acids long. In some embodiments, the imager moiety is about about 5, 8, 9, 10, 11, 12, 13, 14, 15, 18, or 20 nucleic acids long.

In some embodiments, the complementary portions between the imager moiety and the docking moiety may be from about 5 to 20 nucleic acids long, from about 8 to 15, or from about 10 to 12 nucleic acids long nucleic acids long. IN some embodiments, the complementary portions between the imager moiety and the docking moiety may be about 5, 8, 9, 10, 11, 12, 13, 14, 15, 18, or 20 nucleic acids long.

In some embodiments, the nucleic acid imager strand comprises single stranded nucleic acids such as single stranded DNA, RNA, or a nucleic acid analog. A nucleic acid analog may include an altered phosphate backbone, an altered pentose sugar, and/or altered nucelobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the imager moiety is a protein, peptide, or a chemical compound, as a partner to the docking moiety options discussed above in Section I.C above.

Figure 2:
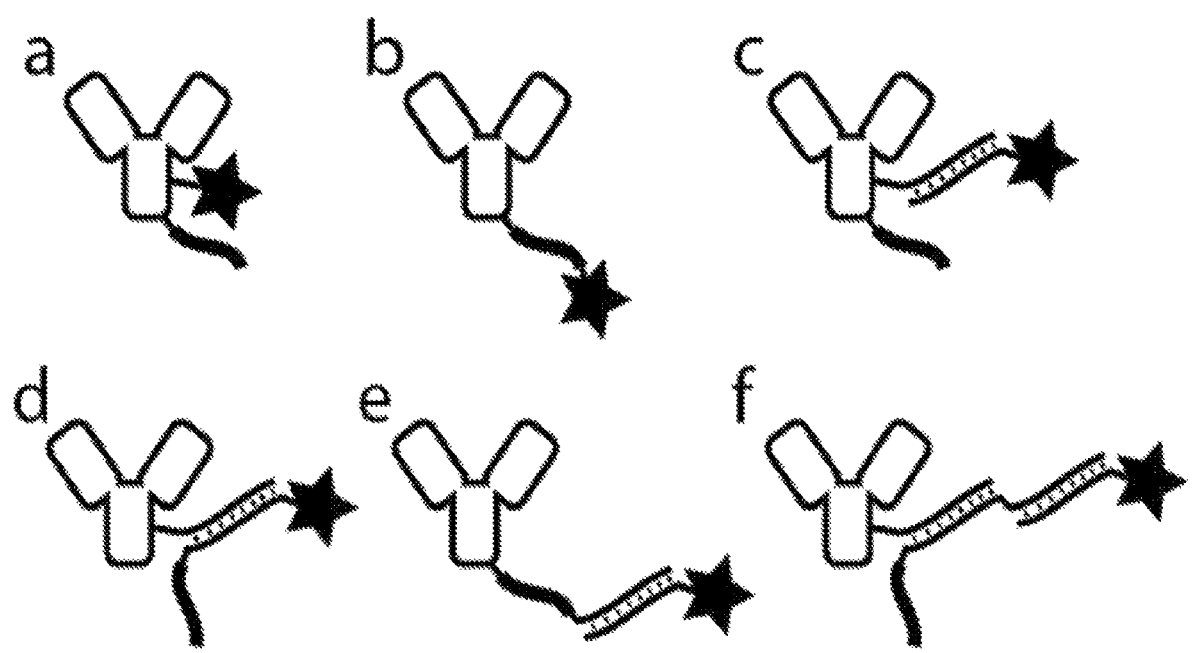
FIGS. 2A-F provide different configurations to attach both non-transiently attached observable moiety (here a fluorescent dye) and a docking moiety to a target recognition moiety (here an antibody).

In some embodiments, such as the embodiment shown in FIG. 2F, the docking moiety may bind to the imager moiety indirectly, such as through an intermediate moiety. For instance, when the docking moiety and the imager moiety are nucleic acids, an intermediate moiety comprising nucleic acids may be used as long as the intermediate moiety has a first region complementary to the docking moiety and a second region complementary to the imager moiety. In this embodiment, it is not necessary for the docking moiety to be complementary to the imager moiety.

II. Methods for Improved Super-Resolution Imaging

In some embodiments, a method of performing super-resolution imaging on a sample comprises (a) contacting the sample with at least one imaging agent comprising (i) a target-recognizing molecule non-transiently attached to at least one observable moiety and (ii) a target-recognizing molecule attached to at least one docking moiety, wherein the docking moiety is capable of transiently binding at least one observable moiety, optionally through an imager moiety; (b) imaging the target-recognizing molecule non-transiently bound to at least one observable moiety; and (c) providing at least one observable moiety capable of transiently binding to the docking moiety, optionally through an imager moiety, and imaging the observable moiety transiently bound to the docking moiety.

In some instances, a method of performing single-molecule localization microscopy comprises (a) providing the imaging agent described herein; (b) obtaining a preview image using at least one observable moiety non-transiently bound to the target recognition moiety; (c) assessing the preview image; and (d) obtaining a single-molecule localization microscopy image using at least one observable moiety transiently bound to the docking moiety.

Any of the imaging agents described in Section I above may be used in these methods.

A. Preview Phase

During the preview phase, the signal observed includes the observable moiety non-transiently bound to the target recognition moiety.

The observable moiety transiently bound to the target recognition moiety may also be generating a signal; however, since such signal and the signal generated by the non-transiently bound observable moiety (which is often much stronger) originate from the same target, it does not substantially change the view seen in the preview phase.

Thus, in the preview phase, it is not necessary to differentiate between the signals provided by the observable moiety non-transiently bound and the observable moiety transiently bound.

B. Terminating the Preview Phase

In many cases, the signal from the preview phase does not interfere with the signal from the super-resolution imaging phase. In these cases, no action is needed to remove or inactivate the non-transiently attached observable moiety used for the preview phase before super-resolution imaging. For example, if the non-transiently attached observable moiety (for diffraction-limited preview) is a green light-emitting fluorophore (e.g., Alexa 488) and the transiently attached observable moiety (for super-resolution imaging) is a near infrared light-emitting fluorophore (e.g., Cy5), one may simply switch the light source and/or filter cube of the microscope from the ones optimized for the green light-emitting fluorophore to the ones optimized for the near infrared light-emitting fluorophore after the preview phase.

In other cases, the signal from the preview phase interferes with the signal from the super-resolution imaging phase. In these cases, the preview phase may be terminated before the super-resolution imaging phase. In these instances, the method further comprising removing or inactivating the observable moiety non-transiently attached to the target recognizing moiety. Thus, in some embodiments, the observable moiety non-transiently bound to the target recognition moiety may be inactivated or removed from the imaging agent, at a desired point in the assay.

The observable moiety may be inactivated by chemical bleaching (e.g., by using an oxidizing reagent such as sodium peroxide) and/or photo bleaching (e.g., by using laser irradiation). Photo bleaching may be done in the presence of the observable moiety transiently bound to the target recognition moiety. This may be accomplished because only the observable moieties in the field of view receive laser irradiation and observable moieties, such as those attached to an imager moiety, elsewhere in the sample are not bleached and can later diffuse to the field of view for super-resolution imaging. While photo bleaching is generally perceived as a negative side effect of imaging, in some embodiments herein it is desired.

The observable moiety may also be removed by introducing a competitor molecule. For example, the target recognizing moiety may be attached to an intermediary moiety hereby called X, and the observable moiety non-transiently attached to it may be attached though another intermediary moiety here called Y, wherein and X and Y interact with strong affinity (dissociation constant lower than or equal to 10 nM). In this case one may introduce another molecule X* which interacts with Y with higher affinity than X, or X* may be introduced at a much higher concentration than X, or both. Given sufficient time, the majority of X will be replaced by X*, and no longer interact with the observable moiety-attached Y (FIG. 3A) Similarly, one may introduce Y* which interacts with X with higher affinity than Y, or introduced at a much higher concentration than X, or both (FIG. 3B). The newly liberated observable moiety may be washed away or kept in solution if its concentration low enough to not interfere with super-resolution imaging as in some embodiments only observable moieties in the field of view will be detected.

Such a method may include nucleic acid strand displacement when the observable moiety non-transiently attached to the target recognizing moiety is attached through a nucleic acid-nucleic acid interaction. Competitor molecules also include streptavidin and/or biotin with different affinities.

For instance, if the target recognizing moiety has a streptavidin conjugated to it and the observable moiety non-transiently attached to it has a biotin conjugated to it, the competitor molecule may be a biotin variant that has a higher affinity for streptavidin than the biotin conjugated to the observable moiety.

In some instances, the observable moiety is inactivated by introducing a fluorescence quencher, including but not limited to Dabsyl, Black Hole Quencher (BHQ-1), BHQ-2, Qxl, Iowa Black FQ, Iowa Black RQ, IRDye QC-1.

If the observable moiety non-transiently bound is attached through a labile bond, such as a photolabile bond, the observable moiety may be removed by cleaving the labile bond. Photolabile bonds may be cleaved by UV irradiation. Other labile bonds may be cleaved chemically.

C. Super-Resolution Imaging Phase

After the observable moiety non-transiently bound to the imaging agent has been removed or inactivated, the super-resolution imaging phase can begin. In this phase, the observable moiety transiently bound to the imaging agent may be observed. This stage may include longer observation times and computer assembly of a final image from blinking or flickering images generated due to the transient binding aspects of the imaging.

If the user determines in the preview phase that the sample is not a desired sample for imaging, the super-resolution imaging phase may not be conducted.

EXAMPLES

Figure 5A:
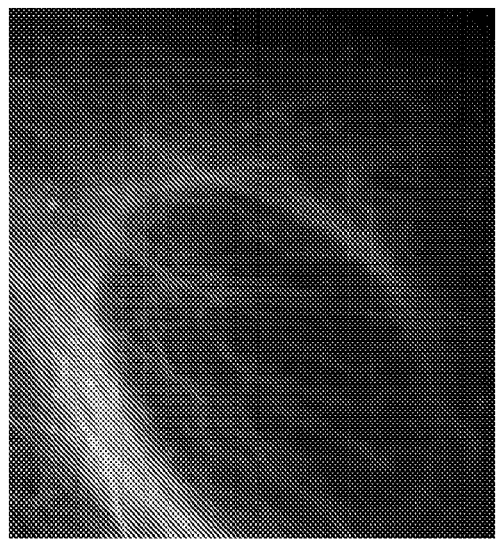
FIGS. 5A-C provide experimental evidence showing the utility of Zoom PAINT in providing a preview of the microtubules in HeLa cells using a two-antibody imaging reagent.
Figure 5B:
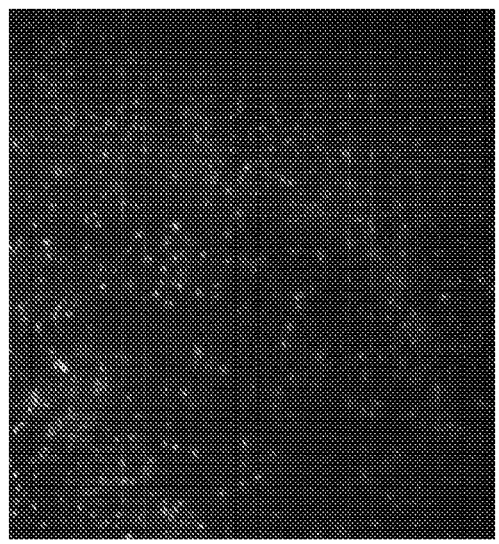
Figure 5C:
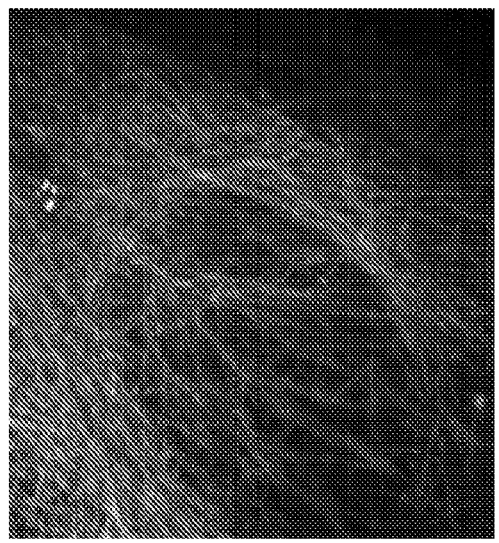

Example 1: Zoom PAINT Provides Preview of HeLa Cells Using a Two-Antibody Imaging Reagent To demonstrate the utility of Zoom PAINT, implemented in the form shown in FIG. 1, we stained HeLa cells (fixed with 3% paraformaldehyde and 0.1% glutaraldehyde, permeabilized and blocked with 3% BSA in 0.2% Triton X-100) with mouse-anti-alpha-tubulin primary antibody (clone DM1A), and then stained the sample with a mixture of Cy5-labeled donkey-anti-mouse antibody (purchased from Jackson ImmunoResearch) and goat-anti-mouse antibody labeled with docking strand P1 (following Jungmann et al., Multiplexed 3D cellular super-resolution imaging with DNA-PAINT and Exchange-PAINT, Nature Methods, 11, 313-318 (2014), Sequence: 5'-TTATACATCTA-3' (SEQ ID NO: 7)), with the final concentration being 5 ug/mL and 20 nM, respectively, for 2 hr. Then, the 'preview' was obtained using 100× 1.49 NA objective, 640 nm laser, and a commercial 'Cy5' filter cube (FIG. 5A). Next, the Cy5 dye on the donkey-anti-mouse antibody was photo-bleached by 640 nm laser at 25 mW for 10 min. Then the imager strand P1* (Sequence: 5'-CTAGATGTAT-Cy3B-3' (SEQ ID NO: 8)) was added to the sample at a final concentration of 0.5 nM. The blinking movie was recorded with 100 ms frame time (see one image collected in FIG. 5B) and the super-resolution image was reconstructed using standard SOFI reconstruction methods (FIG. 5C).

The preview was obtained before the super-resolution imaging was conducted, enabling the user to have significantly more information before investing the time and resources into conducting the super-resolution imaging.

Figure 6A:
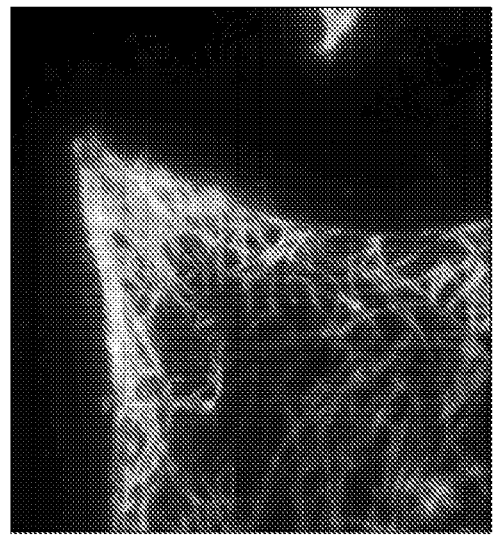
FIGS. 6A-C provide experimental evidence showing the utility of Zoom PAINT in providing a preview of the microtubules in HeLa cells using a single antibody reagent comprising both a fluorophore and a transiently attached imaging agent.
Figure 6B:
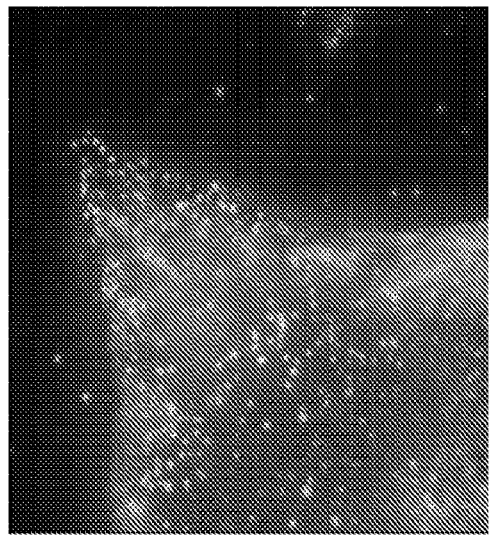
Figure 6C:
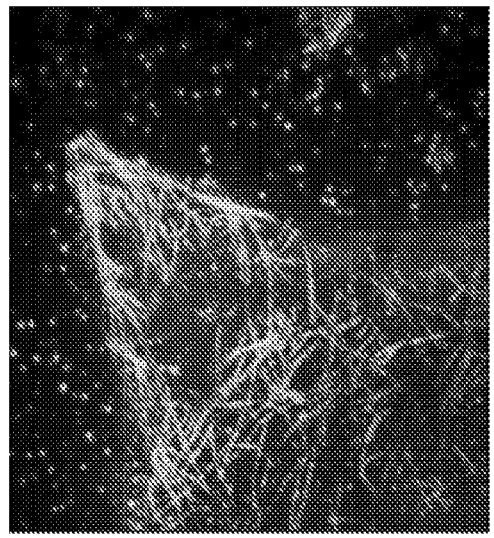

Example 2: Zoom PAINT Provides Imaging Preview of HeLa Cells Using A Single Antibody Reagent Comprising Both a Fluorophore and a Transiently Attached Imaging Agent As an example of Zoom PAINT implemented in the form shown in FIG. 2F, we stained HeLa cells (fixed with 3% paraformaldehyde and 0.1% glutaraldehyde, permeabilized and blocked with 3% BSA in 0.2% Triton X-100) with mouse-anti-alpha-tubulin primary antibody (clone DM1A), and then stained the sample with a DNA-conjugated goat anti-mouse secondary antibody. The DNA on this conjugate was named 'Oligo-1' (docking strand) and had the sequence: 5'-ACTGATTTGGCT-3' (SEQ ID NO: 9). After washing, we treated the sample with 10 nm of Oligo-2 (intermediate strand) and Oligo-3 (imager strand), which had the sequences: 5'-ACTGATTTGGCTTTCGGTAGTAGCT-TATACATCTA-3' (SEQ ID NO: 10) and 5'-GC-CAAATCAGTT-Cy3B-3' (SEQ ID NO: 11), respectively. After washing with PBS, 0.5 nM of imager strand P1* was added to the sample. The sample was first imaged to obtain the preview (FIG. 6A). Then the fluorophore carried by Oligo-3 in field-of-view was photo-bleached with 561 nm laser at 10 mW for 5 min. At this point, the fluorophores carried by the imager strand P1* can be visualized when it binds to Oligo-2 and blinking events can be registered (FIG. 6B) and assembled into a final image (FIG. 6C) using standard SOFI method.

The preview was obtained before the super-resolution imaging was conducted, enabling the user to have significantly more information before investing time and resources into conducting super-resolution imaging.

Example 3: Embodiments

The following numbered items constitute some of the embodiments described herein.

Item 1. An imaging agent comprising:
 a. at least one target recognition moiety;
 b. at least one observable moiety non-transiently bound to the target recognition moiety, and
 c. at least one docking moiety bound to the target recognition moiety, wherein the docking moiety is capable of transiently binding at least one observable moiety.

Item 2. The imaging agent of item 1, wherein the at least one target recognition moiety is an antibody or antigen binding fragment thereof.

Item 3. The imaging agent of any one of items 1-2, wherein the observable moiety non-transiently bound to the target recognition moiety is a signal-emitting moiety.

Item 4. The imaging agent of any one of item 1-3, wherein the signal-emitting moiety is an organic small molecule.

Item 5. The imaging agent of item 4, wherein the organic small molecule is a fluorophore.

Item 6. The imaging agent of any one of items 1-5, wherein the observable moiety non-transiently bound to the target recognition moiety is directly attached to the target recognition moiety.

Item 7. The imaging agent of any one of items 1-5, wherein the observable moiety non-transiently bound to the target recognition moiety is indirectly attached to the target recognition moiety.

Item 8. The imaging agent of item 7, wherein the observable moiety non-transiently bound to the target recognition moiety is directly attached to the docking moiety.

Item 9. The imaging agent of any one of items 1-8, wherein the observable moiety non-transiently bound to the target recognition moiety is bound covalently.

Item 10. The imaging agent of any one of items 1-9, wherein the docking moiety is attached to the imaging agent covalently.

Item 11. The imaging agent of any one of items 1-8 or 10, wherein the observable moiety non-transiently bound to the target recognition moiety is bound noncovalently.

Item 12. The imaging agent of any one of items 1-9 or 11, wherein the docking moiety is attached to the imaging agent noncovalently.

Item 13. The imaging agent of any one of items 1-9 or 11-12, wherein the observable moiety non-transiently bound to the target recognition moiety is bound through a streptavidin-biotin interaction.

Item 14. The imaging agent of any one of items 1-9 or 11-12, wherein the observable moiety non-transiently bound to the target recognition moiety is bound through a nucleic acid-nucleic acid interaction.

Item 15. The imaging agent of item 14, wherein
  a. the nucleic acid bound to the observable moiety is longer than the nucleic acid bound to the target recognition moiety, or
  b. the nucleic acid bound to the target recognition moiety is longer than the nucleic acid bound to the observable moiety, and
the longer nucleic acid serves as a toehold for displacement of the shorter strand.

Item 16. The imaging agent of any one of items 1-15, wherein the docking moiety comprises nucleic acids.

Item 17. The imaging agent of any one of items 1-16, wherein the target recognition moiety is an antibody or antigen binding fragment thereof, an aptamer, or an oligonucleotide.

Item 18. The imaging agent of any one of items 1-17, wherein both the observable moiety non-transiently bound to the target recognition moiety and the observable moiety transiently bound to the target recognition moiety are attached to a single target recognition moiety.

Item 19. The imaging agent of any one of items 1-18, wherein the observable moiety non-transiently bound to the target recognition moiety and the observable moiety transiently bound to the target recognition moiety are attached to different target recognition moieties, wherein:
  a. the different target recognition moieties bind to the same epitope on a target;
  b. the different target recognition moieties bind to different epitopes on the same target;
  c. the different target recognition moieties bind to different proteins, optionally wherein the proteins are capable of interacting with each other.

Item 20. A method of performing super-resolution imaging on a sample comprising:
  a. contacting the sample with at least one imaging agent comprising (i) a target-recognizing molecule non-transiently attached to at least one observable moiety and (ii) a target-recognizing molecule attached to at least one docking moiety, wherein the docking moiety is capable of transiently binding at least one observable moiety;
  b. imaging the target-recognizing molecule non-transiently bound to at least one observable moiety; and
  c. providing at least one observable moiety capable of transiently binding to the docking moiety and imaging the observable moiety transiently bound to the docking moiety.

Item 21. The method of item 20, wherein the target-recognizing molecule is an antibody or antigen binding fragment thereof.

Item 22. The method of any one of items 20-21, wherein the imaging agent is the imaging agent of any one of items 1-19.

Item 23. The method of any one of items 20-22, further comprising removing or inactivating the observable moiety non-transiently attached to the target recognizing molecule.

Item 24. The method of item 23, wherein the observable moiety is inactivated by chemical bleaching.

Item 25. The method of item 23, wherein the observable moiety is inactivated by photo bleaching.

Item 26. The method of item 23, wherein the observable moiety is removed by introducing a competitor molecule.

Item 27. The method of any one of items 23 or 26, wherein the observable moiety is removed by nucleic acid strand displacement.

Item 28. The method of item 23, wherein the observable moiety is inactivated by introducing a fluorescence quencher.

Item 29. A method of performing super-resolution imaging comprising:
  a. providing the imaging agent of any one of items 1-19,
  b. obtaining a preview image using the at least one observable moiety non-transiently bound to the target recognition moiety;
  c. assessing the preview image; and
  obtaining a super-resolution image using at least one observable moiety transiently bound to a docking moiety.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

All of the documents cited herein are incorporated by reference in their entirety for the information for which they are cited.

What is claimed is:

1. A method of performing super-resolution imaging on a sample comprising:
   a. contacting the sample with at least one imaging agent comprising (i) a target recognition moiety non-transiently attached to at least one first observable moiety and (ii) a target recognition moiety attached to at least one docking moiety, wherein the docking moiety is capable of transiently binding at least one second observable moiety;
   b. imaging the target recognition moiety non-transiently bound to at least one first observable moiety; and
   c. providing the at least one second observable moiety capable of transiently binding to the docking moiety and imaging the second observable moiety transiently bound to the docking moiety.

2. The method of claim 1, wherein the target recognition moiety is an antibody or antigen binding fragment thereof.

3. The method of claim 1, wherein the imaging agent is an imaging agent comprising:
   a. at least one target recognition moiety;
   b. at least one first observable moiety non-transiently bound to the target recognition moiety, and
   c. at least one docking moiety bound to the target recognition moiety, wherein the docking moiety is capable of transiently binding at least one second observable moiety.

4. The method of claim 1, further comprising removing or inactivating the observable moiety non-transiently attached to the target recognition moiety.

5. A method of performing super-resolution imaging comprising:

a. providing an imaging agent comprising (a) at least one target recognition moiety; (b) at least one first observable moiety non-transiently bound to the target recognition moiety, and (c) at least one docking moiety bound to the target recognition moiety, wherein the docking moiety is capable of transiently binding at least one second observable moiety, b. obtaining a preview image using the at least one first observable moiety non-transiently bound to the target recognition moiety;

c. assessing the preview image; and d. obtaining a super-resolution image using the at least one second observable moiety transiently bound to the docking moiety.

6. The method of claim 5, wherein the at least one target recognition moiety is an antibody or antigen binding fragment thereof.

7. The method of claim 5, wherein the first observable moiety non-transiently bound to the target recognition moiety is a signal-emitting moiety.

8. The method of claim 7, wherein the signal-emitting moiety is a fluorophore.

9. The method of claim 5, wherein the first observable moiety non-transiently bound to the target recognition moiety is directly attached to the target recognition moiety.

10. The method of claim 5, wherein the first observable moiety non-transiently bound to the target recognition moiety is indirectly attached to the target recognition moiety.

11. The method of claim 10, wherein the first observable moiety non-transiently bound to the target recognition moiety is directly attached to the docking moiety.

12. The method of claim 5, wherein the first observable moiety non-transiently bound to the target recognition moiety is bound covalently.

13. The method of claim 5, wherein the docking moiety is attached to the imaging agent covalently.

14. The method of claim 5, wherein the first observable moiety non-transiently bound to the target recognition moiety is bound noncovalently.

15. The method of claim 5, wherein the docking moiety is attached to the imaging agent noncovalently.

16. The method of claim 14, wherein the first observable moiety non-transiently bound to the target recognition moiety is bound through a nucleic acid-nucleic acid interaction, wherein
    a. the nucleic acid bound to the first observable moiety is longer than the nucleic acid bound to the target recognition moiety, or
    b. the nucleic acid bound to the target recognition moiety is longer than the nucleic acid bound to the first observable moiety, and
the longer nucleic acid serves as a toehold for displacement of the shorter strand.

17. The method of claim 5, wherein the docking moiety comprises nucleic acids.

18. The method of claim 5, wherein the target recognition moiety is an antibody or antigen binding fragment thereof, an aptamer, or an oligonucleotide.

19. The method of claim 5, wherein both the first observable moiety non-transiently bound to the target recognition moiety and the second observable moiety transiently bound to the target recognition moiety are attached to a single target recognition moiety.

20. The method of claim 5, wherein the first observable moiety non-transiently bound to the target recognition moiety and the second observable moiety transiently bound to the docking moiety attached to the target recognition moiety are attached to different target recognition moieties, wherein:
    a. the different target recognition moieties bind to the same epitope on a target;
    b. the different target recognition moieties bind to different epitopes on the same target; or
    c. the different target recognition moieties bind to different proteins, optionally wherein the proteins are capable of interacting with each other.

* * * * *